US012682990B1

(12) United States Patent
Jonak et al.

(10) Patent No.: US 12,682,990 B1
(45) Date of Patent: Jul. 14, 2026

(54) DISTRIBUTED FILE SYSTEM FOR MANAGING PERMISSIONED ACCESS TO RECORDS

(71) Applicant: United Services Automobile Association (USAA), San Antonio, TX (US)

(72) Inventors: Sumita T. Jonak, San Antonio, TX (US); Steven J. Schroeder, Oak Point, TX (US); Ashley Raine Philbrick, San Antonio, TX (US); Emily Kathleen Krebs, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 169 days.

(21) Appl. No.: 18/127,418

(22) Filed: Mar. 28, 2023

Related U.S. Application Data

(63) Continuation of application No. 16/444,773, filed on Jun. 18, 2019, now abandoned.

(Continued)

(51) Int. Cl.
| | |
|---|---|
| *G16H 10/60* | (2018.01) |
| *G06F 21/32* | (2013.01) |

(Continued)

(52) U.S. Cl.
CPC ............. *G16H 10/60* (2018.01); *G06F 21/32* (2013.01); *G06F 21/6245* (2013.01); *H04W 4/029* (2018.02)

(58) Field of Classification Search
CPC ......... G16F 10/60; H04W 4/29; G06F 21/32; G06F 21/6245; G06F 21/6218; G06F 21/62

(Continued)

(56) References Cited

U.S. PATENT DOCUMENTS

| | | | | |
|---|---|---|---|---|
| 7,412,396 B1 * | 8/2008 | Haq | ....................... | G16H 40/67 |
| | | | | 600/300 |
| 8,874,067 B2 * | 10/2014 | Hebbar | ................... | H04L 9/083 |
| | | | | 455/404.1 |

(Continued)

FOREIGN PATENT DOCUMENTS

| | | | | | |
|---|---|---|---|---|---|
| WO | WO-2004102393 A1 * | 11/2004 | ............. | G06Q 20/40 |

OTHER PUBLICATIONS

Spanakis et al., "Secure access to patient's health records using SpeechXRays a mutli-channel biometrics platform for user authentication," IEEE Xplore, 2016.

(Continued)

*Primary Examiner* — Kaylee J Huang
(74) *Attorney, Agent, or Firm* — Fletcher Yoder, PC

(57) ABSTRACT

The distributed file system includes a blockchain node with one or more records recorded in a blockchain of the blockchain node by a series of immutable transactions. More specifically, the blockchain node receives a request to permit access to a record by a service provider. The blockchain node is further configured to determine a geofenced area associated with the service provider, the geofenced area being an area encompassing a geographic location associated with the service provider, and to determine a location of the mobile device associated with the record based on the request. When the blockchain node determines that the mobile device is within the geofenced area associated with the service provider, the blockchain node sends a biometric confirmation request to the mobile device to permit the service provider access to the record.

20 Claims, 5 Drawing Sheets

Related U.S. Application Data

(60) Provisional application No. 62/686,455, filed on Jun. 18, 2018.

(51) Int. Cl.
    *G06F 21/62*          (2013.01)
    *H04W 4/029*        (2018.01)

(58) Field of Classification Search
    USPC .......................................................... 726/4, 7
    See application file for complete search history.

(56) References Cited

U.S. PATENT DOCUMENTS

| | | | | |
|---|---|---|---|---|
| 9,552,684 | B2 | 1/2017 | Bacco et al. | |
| 10,446,267 | B2 * | 10/2019 | Fuhrmann | H04L 51/56 |
| 10,909,582 | B1 * | 2/2021 | Brandt | G06Q 40/03 |
| 2004/0111622 | A1 * | 6/2004 | Schoenberg | G16H 10/60 |
| | | | | 713/182 |
| 2008/0208943 | A1 * | 8/2008 | Haneda | H04N 21/84 |
| | | | | 375/E7.009 |
| 2009/0276243 | A1 * | 11/2009 | Fotsch | G16H 50/80 |
| | | | | 715/205 |
| 2013/0144637 | A1 | 6/2013 | Bertha et al. | |
| 2015/0046984 | A1 * | 2/2015 | Belton, Jr. | H04L 63/10 |
| | | | | 726/4 |
| 2015/0089244 | A1 * | 3/2015 | Roth | H04L 9/3226 |
| | | | | 713/193 |
| 2015/0220931 | A1 * | 8/2015 | Alsina | G06Q 20/04 |
| | | | | 705/44 |
| 2016/0301691 | A1 * | 10/2016 | Miller | H04L 63/0815 |
| 2016/0359799 | A1 * | 12/2016 | Jones | G06F 21/604 |
| 2017/0091397 | A1 * | 3/2017 | Shah | H04L 63/20 |
| 2017/0148240 | A1 * | 5/2017 | Kovacs | G01G 23/36 |
| 2017/0155630 | A1 * | 6/2017 | East | H04L 63/08 |
| 2017/0161439 | A1 * | 6/2017 | Raduchel | G16H 10/60 |
| 2018/0060496 | A1 * | 3/2018 | Bulleit | H04L 9/0643 |
| 2018/0182052 | A1 | 6/2018 | Panagos | |
| 2018/0211059 | A1 * | 7/2018 | Aunger | H04L 63/166 |
| 2018/0308566 | A1 | 10/2018 | Dempers et al. | |
| 2019/0158487 | A1 * | 5/2019 | Hayes | H04L 63/0861 |
| 2019/0349372 | A1 * | 11/2019 | Smith | G06F 21/31 |
| 2019/0370500 | A1 * | 12/2019 | Lee | G06Q 40/03 |
| 2020/0176094 | A1 * | 6/2020 | Ury | G16B 50/30 |

OTHER PUBLICATIONS

Huetado et al., "Interaction Evaluation of a Mobile Voice Authentication System," IEEE Xplore, 2016, School of Engineering and Digital Arts, University of Kent, Canterbury, United Kingdom.
Google patents search, Sep. 20, 2021 (Year: 2021).
ip.com search, Mar. 15, 2022 (Year: 2022).
ip.com search, Jun. 11, 2022 (Year: 2022).

\* cited by examiner

180

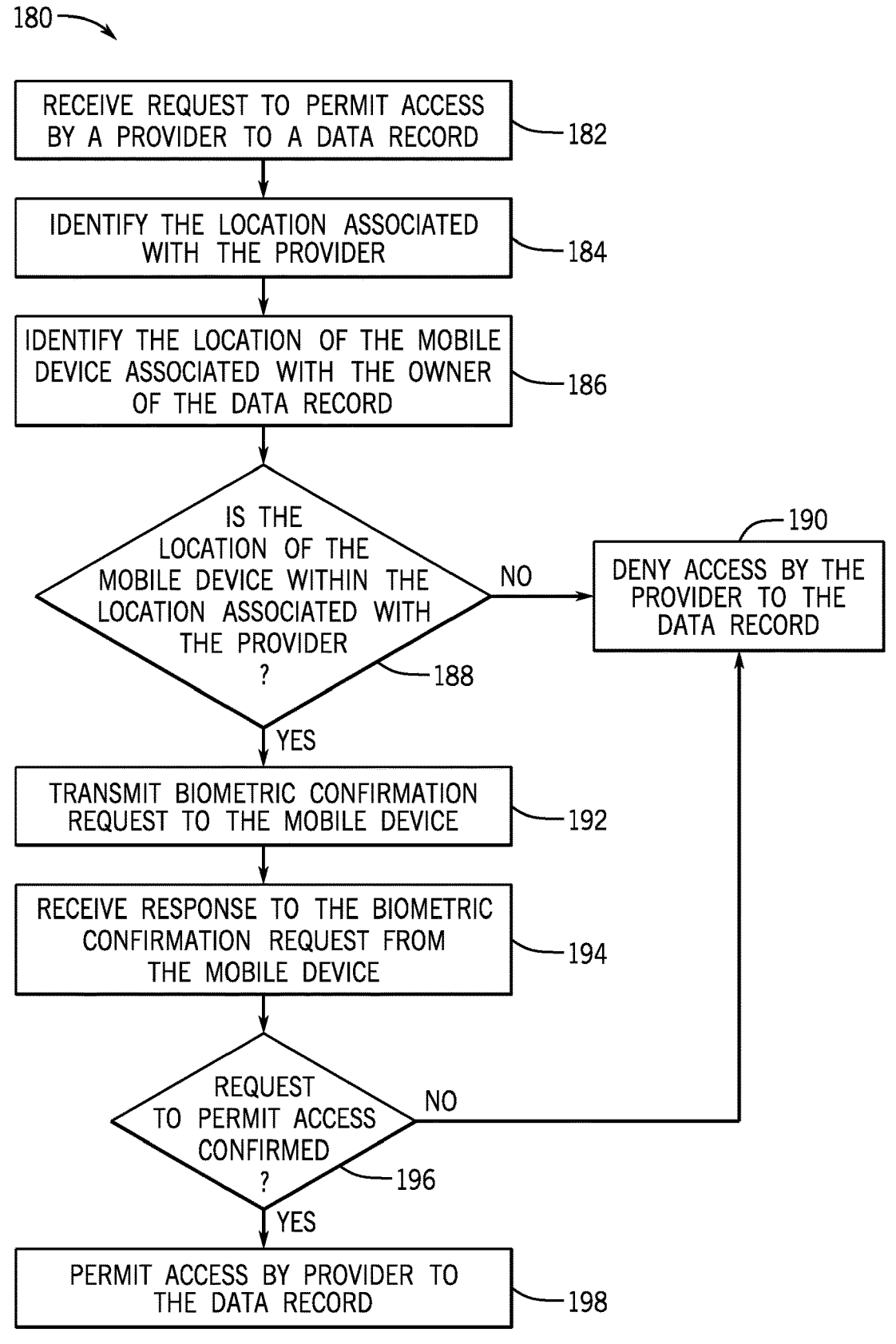

RECEIVE REQUEST TO PERMIT ACCESS BY A PROVIDER TO A DATA RECORD —182

IDENTIFY THE LOCATION ASSOCIATED WITH THE PROVIDER —184

IDENTIFY THE LOCATION OF THE MOBILE DEVICE ASSOCIATED WITH THE OWNER OF THE DATA RECORD —186

IS THE LOCATION OF THE MOBILE DEVICE WITHIN THE LOCATION ASSOCIATED WITH THE PROVIDER ? —188

NO

DENY ACCESS BY THE PROVIDER TO THE DATA RECORD —190

YES

TRANSMIT BIOMETRIC CONFIRMATION REQUEST TO THE MOBILE DEVICE —192

RECEIVE RESPONSE TO THE BIOMETRIC CONFIRMATION REQUEST FROM THE MOBILE DEVICE —194

REQUEST TO PERMIT ACCESS CONFIRMED ? —196

NO

YES

PERMIT ACCESS BY PROVIDER TO THE DATA RECORD —198

FIG. 4

DISTRIBUTED FILE SYSTEM FOR MANAGING PERMISSIONED ACCESS TO RECORDS

CROSS-REFERENCE TO RELATED APPLICATIONS

This application is a continuation of U.S. application Ser. No. 16/444,773, entitled "Permissioned Access Systems and Methods," filed Jun. 18, 2019, which claims priority to and the benefit of U.S. Provisional Patent Application No. 62/686,455, entitled "Permissioned Access Systems and Methods," filed Jun. 18, 2018, each of which is herein incorporated by reference in its entirety for all purposes.

BACKGROUND

The present disclosure relates generally to electronic medical records. More specifically, the present disclosure relates to systems and methods for providing permissioned access to electronic records stored in a distributed file system.

The present disclosure relates generally to electronic medical records. More specifically, the present disclosure relates to systems and methods for providing permissioned access to electronic records stored in a distributed file system.

Electronic records, such as electronic medical records, electronic financial records, electronic credit records, and/or the like may include sensitive information related to a user. For example, medical records may include sensitive information associated with a patient, such as information identifying the patient, a medical history of the patient, health insurance information associated with the patient, and/or the like. Accordingly, regulatory requirements, such as the Health Insurance Portability and Accountability Act of 1996 (HIPPA), may provide specific instructions regarding the retention, distribution, use, and/or modification, among other things, of the electronic records. However, maintaining control over the access, use, distribution, and/or retention of electronic copies of records associated with the user may be cumbersome to implement. Further, in some cases, a number of different service and/or healthcare providers, such as physicians, emergency clinics, pharmacies, and/or health insurance companies, may use electronic records to service the user, which may increase the complexity of providing secure access to these records.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method is performed by at least one processor, the method including receiving, at a blockchain node of a distributed file system comprising one or more records associated with a user, a request to permit access to a record of the one or more records by a service provider. The request includes a record identifier associated with the record, an indication of a location of the service provider, and an indication of a location of a mobile device associated with an owner of the record, and wherein the one or more records are stored in a blockchain of the blockchain node by a series of immutable transactions. Furthermore, the method includes identifying the record stored in the blockchain based on the record identifier. The method also includes determining a geofenced area associated with the service provider based on the indication of the location of the service provider, wherein the geofenced area corresponds with an area encompassing a geographic location associated with the service provider. Moreover, the method includes determining a location of the mobile device based on the indication of the location of the mobile device, and determining that the mobile device is within the geofenced area associated with the service provider. In addition, the method includes, sending a biometric confirmation request to the mobile device for a biometric confirmation to permit the service provider access to the record based on the mobile device being within the geofenced area, receiving the biometric confirmation from the mobile device, and upon receiving the biometric confirmation, transmitting the record or a reference to the record from the blockchain to a service provider device associated with the service provider according to permission information associated with the record.

In another embodiment, a distributed file system includes a blockchain node comprising one or more records associated with a user, wherein the one or more records are recorded in a blockchain of the blockchain node by a series of immutable transactions. Furthermore, the distributed file system includes a processor configured to receive a request to permit access to a record of the one or more records by a service provider, wherein the request comprises a record identifier associated with the record, an indication of a location of the service provider, and an indication of a location of a mobile device associated with an owner of the record. The processor further configured to identify the record stored in the blockchain based on the record identifier, and determine a geofenced area associated with the service provider based on the indication of the location of the service provider, wherein the geofenced area corresponds with an area encompassing a geographic location associated with the service provider. In addition, the processor is configured to determine a location of the mobile device based on the indication of the location of the mobile device, determine that the mobile device is within the geofenced area associated with the service provider, and send a biometric confirmation request to the mobile device for a biometric confirmation to permit the service provider access to the record based on the mobile device being within the geofenced area. The processor is configured to receive the biometric confirmation from the mobile device, and upon receiving the biometric confirmation, transmit the record or a reference to the record from the blockchain to a service provider device associated with the service provider according to permission information associated with the record.

In another embodiment, a tangible, non-transitory, machine-readable medium, includes machine-readable instructions which, when executed, cause at least one processor to perform operations comprising, receiving, at a blockchain node of a distributed file system comprising one or more records associated with a user, a request to permit access to a record of the one or more records by a service provider, wherein the request comprises a record identifier associated with the record, an indication of a location of the service provider, and an indication of a location of a mobile device associated with an owner of the record, and wherein the one or more records are stored in a blockchain of the blockchain node by a series of immutable transactions. The operations further including identifying the record stored in the blockchain based on the record identifier, and determining a geofenced area associated with the service provider based on the indication of the location of the service provider, wherein the geofenced area corresponds with an area encompassing a geographic location associated with the service provider. Moreover, the operations include determining a location of the mobile device based on the indication of the location of the mobile device, determining that the mobile device is within the geofenced area associated with the service provider, and transmitting a biometric confirmation request to the mobile device for a biometric confirmation to permit the service provider access to the record based on the mobile device being within the geofenced area. The operations include receiving the biometric confirmation from the mobile device, and upon receiving the biometric confirmation, transmitting the record or a reference to the record from the blockchain to a service provider device associated with the service provider according to permission information associated with the record.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 4 is a flow diagram of a method for receiving and responding to a request to permit access by a healthcare provider to a data record stored in the distributed file system of FIG. 2, in accordance with embodiments described herein.

DETAILED DESCRIPTION

Figure 1:
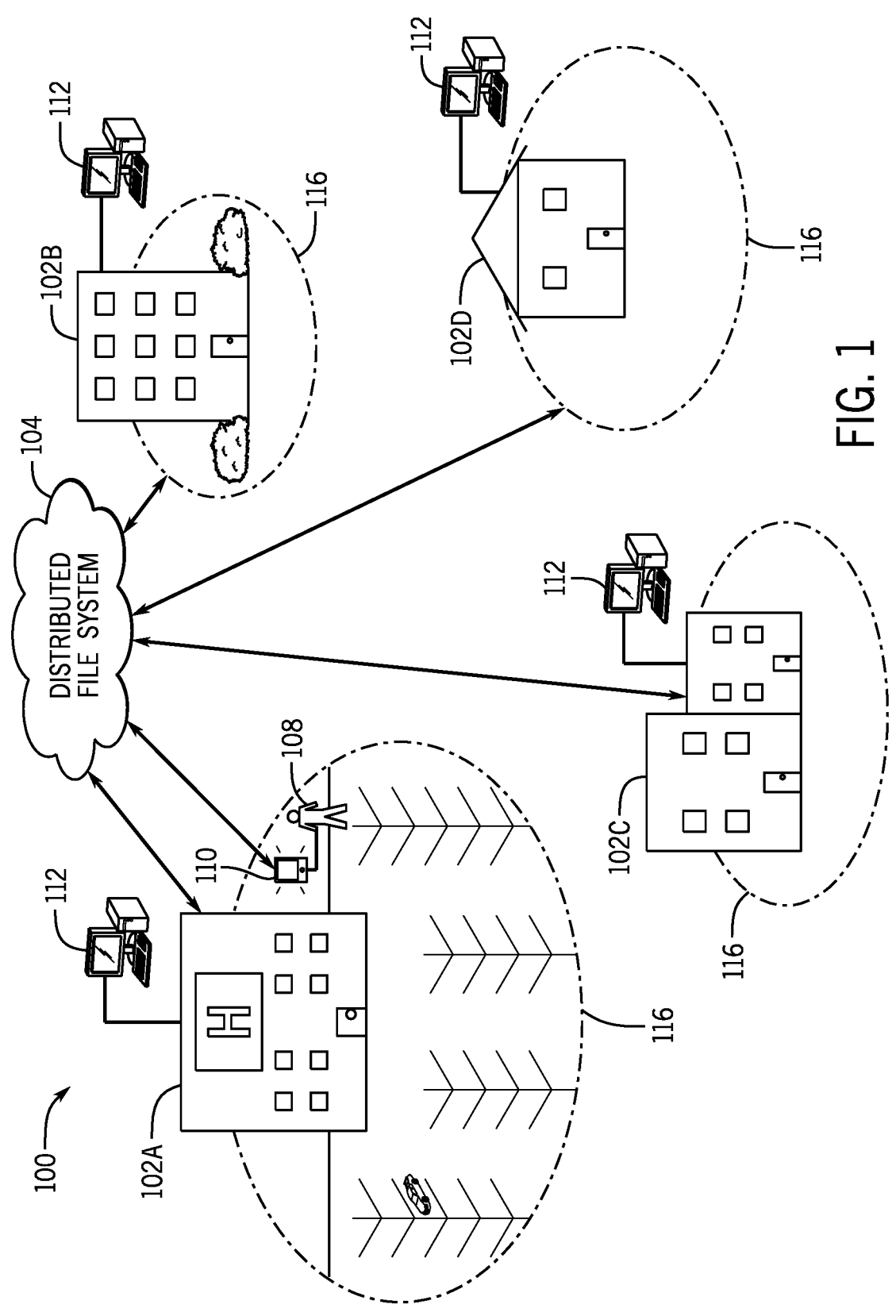
FIG. 1 is a schematic diagram of a healthcare network, in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates generally to improved systems and methods for managing permissioned access to data records stored in a distributed file system. More specifically, certain embodiments are directed to implementing ephemeral permissioned access by a healthcare provider to electronic medical records stored in the distributed file system. In some embodiments, a healthcare network may include one or more healthcare providers (e.g., service providers), such as physicians, emergency clinics, pharmacies, and/or health insurance companies, which may service a patient based in part on electronic medical records associated with the patient and which may in turn update (i.e., write to) those records based on the service(s) provided.

As the electronic medical records may include sensitive information related to the patient, such as a medical history of the patient and/or information related to the patient protected under HIPPA, the access by the one or more healthcare providers may be restricted based on one or more factors. More specifically, in some embodiments, to provide temporary access by one of the one or more healthcare providers to the electronic medical records, the patient may provide ephemeral permissions to the healthcare provider that may expire after an event, such as a set period of time elapses, a number of instances of access to the electronic medical records by the healthcare provider has been exceeded, and/or the location of a mobile device associated with the patient is determined to be outside a location associated with the healthcare provider.

Further, in some embodiments, the electronic medical records may be stored in a distributed file system, such as a distributed ledger and/or blockchain, where the electronic medical records may be encrypted. Accordingly, controlling permissions and/or access to the electronic records may involve selectively allowing a computing device associated with the healthcare provider to access and/or decrypt the distributed file system based on an input, such as a biometric confirmation, received from a mobile device associated with the patient at the distributed file system. Moreover, using the distributed file system, the healthcare provider may be limited to accessing a reference to the electronic medical records instead of the raw data associated with the electronic medical records, which may limit unauthorized reproduction of the electronic medical records.

Accordingly, the present disclosure provides techniques to facilitate increased control and/or security over the retention, distribution, and/or management of data records. For example, by providing ephemeral permissions to a healthcare provider to access electronic medical records, the healthcare provider may be granted limited exposure and/or control over the electronic medical records. Further, by providing a reference to the data record, the original data record may remain uncorrupted in the distributed file system. Additionally, by validating permissions granted by the patient based on a biometric confirmation, the identity of the patient granting the permissions may be confirmed. Thus, at least in some instances, the techniques described herein may protect the data records stored in the distributed file system from corruption and/or unauthorized use and/or distribution. In addition, the present techniques are more convenient for the patient, because the patient may not personally store the electronic medical records. In addition, the access to the electronic medical records may be managed via the patient's own device instead of via unfamiliar access points or patient portals on the provider side.

Turning now to the drawings, FIG. 1 is a schematic diagram of a healthcare network 100, which may include a healthcare provider 102 (e.g., service provider), a distributed file system 104, a patient 108 (e.g., user) associated with a user mobile device 110, and/or the like. In some embodiments, the patient 108 may own and/or control access to electronic medical records, which may be stored in the distributed file system 104 and accessed by the patient 108 via the user mobile device 110, as described in greater detail below. The electronic medical records may include, for example, information related to the patient, such as identification information (e.g., a name, a social security number, and/or the like), health insurance information, medical data (e.g., medical image data, laboratory data), and/or a medical history of the patient 108.

To provide information associated with the patient included in the electronic medical records, such as the medical history of the patient 108, the patient 108 may grant permissions to access the electronic medical records. In some embodiments, for example, the patient 108 may grant the healthcare provider 102 permissions to access the electronic medical records to diagnose and/or treat the patient 108. In such cases, depending on the permissions granted by the patient, the healthcare provider 102 may generate, access, and/or update the electronic medical records associated with the patient. Accordingly, the healthcare provider 102 may include a provider computing device 112 implemented to communicate with the distributed file system 104 to generate, access, and/or update the electronic medical records associated with the patient.

In some embodiments, to grant permissions to access the electronic medical records, the patient may generate, via the user mobile device 110, a request to permit access to the healthcare provider 102. Additionally or alternatively, the user may receive, at the user mobile device 110, a request to gain access to the electronic medical records generated by the healthcare provider 102 at the provider computing device 112. In any case, to verify that the permissions to access the electronic medical records are approved, the patient may provide a confirmation, such as a biometric confirmation (e.g., a fingerprint, a facial scan, voice recognition, eye scan (e.g., retinal and/or iris scan), and/or the like), at the user mobile device 110.

After receiving the confirmation provided by the patient to grant the healthcare provider 102 permissions to access the electronic medical records, the healthcare provider 102 may access, via the provider computing device 112, the electronic medical records. More specifically, in some embodiments, the provider computing device 112 may access a reference (e.g., pointer) to the electronic medical records stored at the distributed file system 104. In such cases, because the provider computing device 112 may not access the raw data associated with the electronic medical records, the number of copies of the raw data may be limited. Accordingly, the provider computing device 112 may be prevented from distributing additional copies of the electronic medical records to, for example, a computing device lacking permissions to access the electronic medical records. Additionally or alternatively, the raw data associated with the electronic medical records may be obtained at the provider computing device 112. However, in some embodiments, the raw data obtained by the provider computing device 112 may remain valid (e.g., incorruptible) and/or accessible for a limited period of time, as may be specified by the patient.

Further, in some embodiments, the patient 108 may grant ephemeral (e.g., temporary) permissions to access the electronic medical records that may expire after a set period of time elapses, a number of instances of access to the electronic medical records by the healthcare provider 102 have been exhausted, a geographic location of the user mobile device 110 is determined to be outside a specified area, and/or the like. For example, in some embodiments, the patient 108 may grant permissions to the healthcare provider 102 to access the electronic medical records that remain valid for a set time period (e.g., two weeks), and after the time period has elapsed, the healthcare provider 102 may be barred from accessing the electronic medical records. Additionally or alternatively, the patient 108 may grant permissions that allow the healthcare provider 102 to access the electronic medical records for a finite number of instances (e.g., five accesses to the electronic medical records).

Further, in some embodiments, the geographic location of the user mobile device 110, which may correspond to the location of the patient 108, may be used to govern permissions to access the electronic medical records. For example, in some embodiments, the patient 108 may grant permission to access the electronic medical records to the healthcare provider 102 that may remain valid while a geographic location of the user mobile device 110 is determined to be within a geofenced area 116 encompassing the healthcare provider 102 and may expire after the user mobile device 110 exits the geofenced area 116. Further, in some embodiments, the permissions may revalidate after the user mobile device 110 is determined to have returned to the geofenced area 116.

The geographic location of the user mobile device 110 may be determined based on, for example, location information provided by a global positioning system (GPS) sensor in the user mobile device 110. Further, the geofenced area 116 may correspond to an approximate geographic location associated with the healthcare provider 102, such as within a hundred yard radius of the healthcare provider 102, and may be determined based in part on stored information related to the healthcare provider 102, an Internet Protocol (IP) address of the provider computing device 112, and/or the like, as discussed in greater detail below.

While the ephemeral permissions are described above as expiring after an event, such as when the set time period elapses, the number of instances of access is exceeded, or the geographic location of the user mobile device 110 is determined to be outside the geofenced area 116, in some embodiments, the ephemeral permissions may expire after any combination of these events. Further, in some embodiments, the patient 108 may grant ephemeral permissions that expire whenever the first of the set time period elapses, the number of instances of access is exceeded, or the geographic location of the user mobile device 110 is determined to be outside the geofenced area 116.

In some embodiments, the healthcare network 100 may include multiple healthcare providers 102. Further, different information in the electronic medical records may be used by each healthcare provider 102. For example, a first healthcare provider 102A may access a first subset of information from the electronic medical records, such as information related to the vision history of the patient 108, while a second healthcare provider 102B may access a second subset of information from the electronic medical records, such as information related to X-ray scans of the patient 108.

Accordingly, in some embodiments, the patient 108 may grant first permissions to the first healthcare provider 102A to provide access by the first healthcare provider 102A to the first subset of information, while blocking access by the first healthcare provider 102A to the second subset of information. Further, the patient 108 may grant second permissions to the second healthcare provider 102B to provide access by the second healthcare provider 102B, while blocking access by the second healthcare provider 102B to the first subset of information. It should be understood that the healthcare network 100 may include the individual healthcare providers 102 of each patient 108, which may or may not be in association with one another. Accordingly, as provided herein, the patient 108 may manage access to electronic medical records across different types of providers 102 that may or may not communicate with one another.

Figure 2:
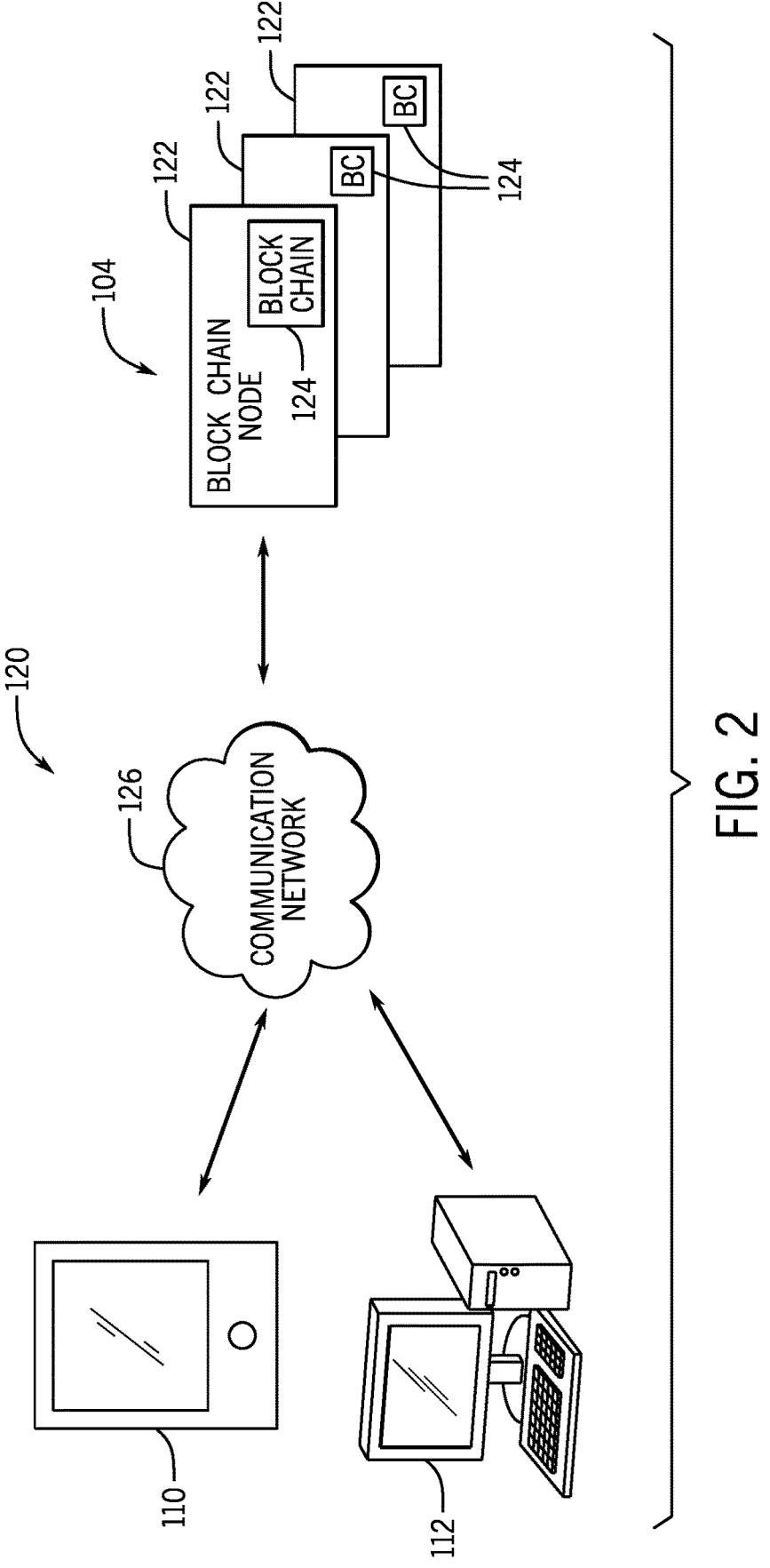
FIG. 2 is a data flow diagram illustrating communication between a distributed file system and one or more computing devices that may be part of the healthcare network of FIG. 1, in accordance with embodiments described herein.

Turning now to FIG. 2, a data flow diagram 120 provides a more detailed illustration of communication between the user mobile device 110, the provider computing device 112, and the distributed file system 104. In some embodiments, the distributed file system 104 may be hosted on a peer-to-peer network and may be implemented as a distributed ledger, such as blockchain. Accordingly, the distributed file system 104, may include one or more blockchain nodes 122 (e.g., computing systems) communicatively coupled to one another to implement the peer-to-peer network. Each of the one or more blockchain nodes 122 may include a copy (e.g., instance) of a blockchain 124. The blockchain 124 may include the electronic medical records, which may be recorded in the blockchain 124 by a series of immutable transactions.

Further, in some embodiments, the distributed file system 104 may be implemented and/or hosted using an interplanetary file system (IPFS). Using IPFS protocol and/or another suitable protocol, the distributed file system 104 may store a set of hashed data, such as hashed electronic medical records. Further, to maintain a set of permissions and/or restricted access to a set of data, such as the electronic medical records, stored in the distributed file system 104, the distributed file system 104 may be implemented to encrypt the set of data based on, for example, public-key cryptography (e.g., a public and private key pair). Accordingly, because the electronic medical records may be stored in the distributed file system 104, the patient 108 may utilize these protocols to own and control (e.g., restrict) access to the electronic medical records. More specifically, in some embodiments, the patient 108 may facilitate compliance with HIPPA requirements by the healthcare provider 102 by, for example, managing the retention of the electronic medical records stored in the distributed file system 104, restricting access to the electronic medical records stored in the distributed file system 104, and/or controlling distribution of the electronic medical records stored in the distributed file system 104.

To communicate with and/or access data stored on the distributed file system 104, the user mobile device 110 and/or the provider computing device 112 may communicatively couple to the distributed file system 104 via a communication network 126, such as a local area network (LAN), a wide area network (WAN) (e.g., the Internet), and/or the like. Accordingly, in some embodiments, a hypertext transfer protocol (HTTP) or a hypertext transfer protocol secure (HTTPS) request may be transmitted from and/or received at the user mobile device 110 and/or the provider computing device 112 via the communication network 126 to facilitate communication with the distributed file system 104. Further, in some embodiments, a graphical user interface, such as an application, and/or a web browser may be displayed on the user mobile device 110 and/or the provider computing device 112 to facilitate user (e.g., patient 108 and/or healthcare provider 102) interaction with the distributed file system 104 via the communication network 126. Accordingly, the user mobile device 110 and/or the provider computing device 112 may include one or more input structures, such as a keyboard, a mouse, a touch screen display, and/or the like, to facilitate interaction with the graphical user interface.

While the embodiments described herein involve electronic medical records accessed by the patient 108 and/or the healthcare provider 102, any suitable data may be stored in the distributed file system 104 and/or accessed by any suitable computing device associated with a user and/or a service provider. For example, a user may additionally or alternatively store and control permissions to access credit data, financial data, sensitive information, and/or any other information in the distributed file system 104. Accordingly, the embodiments described herein are intended to be illustrative and not limiting.

Figure 3:
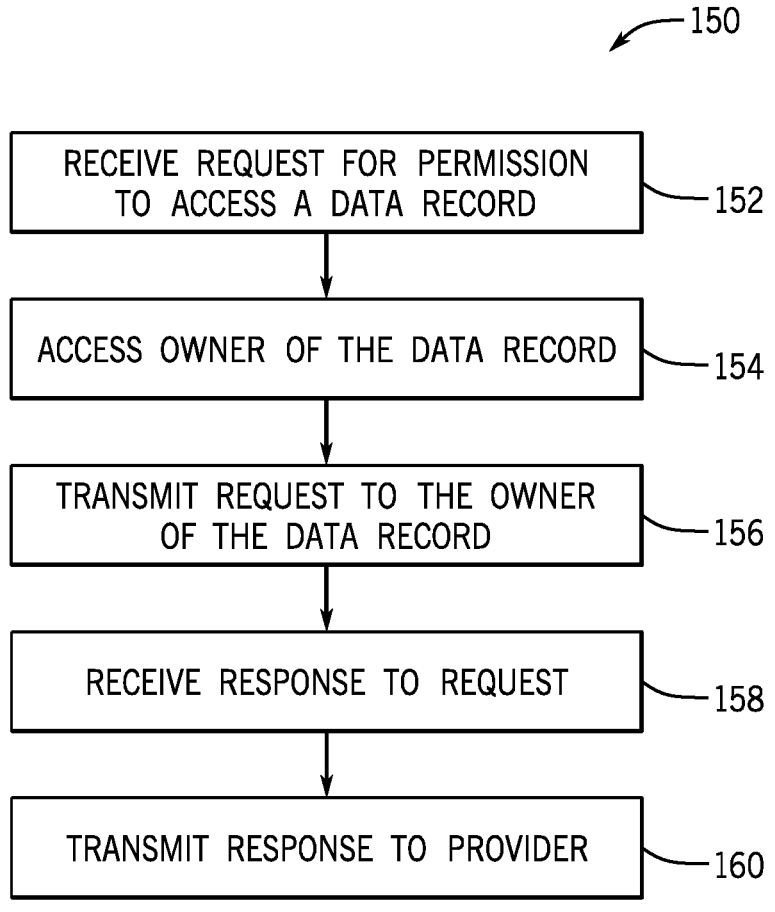
FIG. 3 is a flow diagram of a method for receiving and responding to a request to gain access to a data record stored in the distributed file system of FIG. 2, in accordance with embodiments described herein.

With the foregoing in mind, FIG. 3 illustrates a method 150 for receiving and responding to a request to gain access to a data record stored in the distributed file system 104, in accordance with embodiments described herein. Although the following description of the method 150 is described in a particular order, which represents a particular embodiment, it should be noted that the method 150 may be performed in any suitable order. Further, certain steps may be skipped altogether, and additional steps may be included in the method 150. Moreover, although the following description of the method 150 is described as being performed by a blockchain node 122, it should be noted that the method 150 may be performed by other implementations of the distributed file system 104 or any suitable computing device. More specifically, in some embodiments, the method 150 may be implemented by a processor, which is understood to include one or more processors.

To initiate the method 150, a request for permission to access a data record may be received (process block 152). In some embodiments, the request may originate from the provider computing device 112 and, as illustrated in the data flow diagram 120, be transmitted to the distributed file system 104 via the communication network 126. Further, the request may include information identifying the data record (e.g., record identifier), such as the electronic medical records or a portion of the electronic medical records. In the case of a distributed file system 104 implemented with IPFS, for example, the information identifying the data record may include a hash address of the data record. Additionally or alternatively, the request may include information identifying the healthcare provider 102 associated with the provider computing device and/or identifying the geofenced area 116 encompassing the geographic location of the healthcare provider 102. Further, the request may include information regarding the extent of the permissions requested. That is, for example, the request may specify whether read-only permissions, read-write permissions, and/or the like are suitable for the requested access to the data record. Additionally or alternatively, the request may include one or more parameters associated with ephemeral permissions to the data record, which may be set as default parameters, specified by the healthcare provider 102, and/or specified and/or modified by the owner of the data record. Accordingly, the request may limit requested access to the data record based on a set time period (e.g., two weeks), based on a geographic location of the provider computing device 112 and/or the user mobile device 110, based on a number of instances of access, and/or the like, as specified by the healthcare provider 102, the default parameters, and/or the owner of the data record.

After receiving the request for permission to access the data record, the blockchain node 122 may access the owner of the data record (process block 154). Accordingly, based on information included in the request, such as the hash address of the data record, the data record may be accessed and the owner of the data record may be identified. More specifically, in some embodiments, the blockchain node 122 may access the user mobile device 110 associated with the owner of the data record, such as the patient 108, from the identified data record.

Accordingly, after accessing the owner of the data record, the blockchain node 122 may transmit the request to the owner (e.g., to the user mobile device 110 associated with the owner) (process block 156). The request may be sent to the user as a notification, which may include a visualization depicted on a display of the user mobile device 110 to convey details of requested permissions included in the request and/or information identifying the healthcare provider 102. The notification may be delivered to the user mobile device 110 via short messaging service (SMS) (e.g., text message), an application alert, an electronic mail (e.g., e-mail) message, or a combination thereof. After receiving the notification, the user mobile device 110 may provide an indication to the owner of the data record that the notification was received. The indication may be a ring tone, a vibration pattern, a visualization, and/or the like. Further, in some embodiments, the indication may activate an application or program stored on the user mobile device 110 despite the user mobile device 110 being in a sleep or low power mode to increase the likelihood that the owner will take note of the notification.

A response to the request may then be received at the blockchain node 122 (process block 158). In some embodiments, the blockchain node 122 may receive the response from the user mobile device 110. Further, the response may include information approving, denying, and/or modifying the request for permission to access the data record. That is, for example, in some embodiments, the owner of the data record may fully approve or fully deny the entire request for permission. Additionally or alternatively, the owner may approve a portion of the request for permission, deny the remaining portion of the request, modify the portion of the request, or a combination thereof. Approving a request may grant the requested permissions to access the data record to the healthcare provider 102, and denying the request may block the healthcare provider 102 from receiving the requested permissions to access the data record, which may subsequently block the healthcare provider 102 from accessing the data record. Further, in some embodiments, modifying the request may, involve updating the level of extent of the permissions granted to the healthcare provider 102. For example, the request may specify that read-write permissions are requested, while a response may modify the request to only grant read-only permissions to the data record. Additionally or alternatively, a request for read-only permissions may be modified to grant read-write permissions.

The response may further include ephemeral permissions associated with any access granted to the healthcare provider 102. That is, for example, the patient 108 and/or the healthcare provider 102 may specify an event, such as a set time period elapsing, a number of instances of access to the data record being exceed, and/or detection of the user mobile device 110 outside the geofenced area 116 associated with the healthcare provider 102, which may cause the permissioned access to expire and/or become invalid. Additionally or alternatively, the user mobile device 110 may automatically apply the ephemeral permissions to the request and/or the blockchain node 122 may automatically associate ephemeral permissions with the request. Accordingly, approving, denying, and/or modifying the request in the response may involve approving, denying, and/or updating the ephemeral permissions specified in the request and/or applied by default.

Further, the response may include a validation received at the user mobile device 110 from the owner confirming the response. In some embodiments, for example, the validation may include a multi-factor (e.g., two-factor) authentication of the identity of the owner, which may confirm the response is received from the owner and/or that the request was transmitted to an appropriate user mobile device 110. Additionally or alternatively, the validation may include a biometric confirmation, such as a fingerprint scan, a voice recognition scan, an eye scan, and/or a facial scan, which may confirm the identity of the owner.

The received response may then be transmitted to the healthcare provider 102 (e.g., to the provider computing device 112) (process block 160). The response may be sent to the healthcare provider 102 as a notification, which may include a visualization depicted on a display of the provider computing device 112 to convey details of the approved, denied, and/or modified permissions provided to the healthcare provider 102. The notification may be delivered to the provider computing device 112 via short messaging service (SMS) (e.g., text message), an application alert, an electronic mail (e.g., e-mail) message, or a combination thereof. After receiving the notification, the provider computing device 112 may provide an indication to the healthcare provider 102 that the notification was received. The indication may be a ring tone, a vibration pattern, a visualization, and/or the like. Further, in some embodiments, the indication may activate an application or program stored on the provider computing device 112 despite the provider computing device 112 being in a sleep or low power mode to increase the likelihood that the healthcare provider 102 will take note of the notification.

Further, in some embodiments, if the response indicates that any portion of the request has been approved, the response, when transmitted to the healthcare provider 102, may include information, such as a public key or a private key, which may be used by the provider computing device 112 to subsequently access and/or decrypt the data record. Additionally or alternatively, the public key and/or private key may be associated with the healthcare provider 102 in the distributed file system 104 and accessed at the distributed file system 104 in response to a request to access a data record by the healthcare provider 102.

To illustrate further, FIG. 4 is a method 180, which may be an embodiment of method 150, to receive and respond to a request to permit access by a healthcare provider 102 to a data record. Although the following description of the method 180 is described in a particular order, which represents a particular embodiment, it should be noted that the method 180 may be performed in any suitable order. Further, certain steps may be skipped altogether, and additional steps may be included in the method 180. Moreover, although the following description of the method 180 is described as being performed by the blockchain node 122, it should be noted that the method 180 may be performed by other implementations of the distributed file system 104 or any suitable computing device. More specifically, in some embodiments, the method 180 may be implemented by a processor, which is understood to include one or more processors.

The method 180 may be initiated after a request to permit access by a provider (e.g., healthcare provider 102) to a data record (e.g., the electronic medical records) is received at the blockchain node 122 (process block 182). In some cases, the request may be received from the provider computing device 112, which may indicate, for example, that the healthcare provider 102 is requesting permission to access the data record. Additionally or alternatively, the request may be received from the user mobile device 110. A request received from the user mobile device 110 may indicate that the patient 108 (e.g., owner) is requesting to grant access to the healthcare provider 102. Further, the owner may initiate transmitting the request via the graphical user interface provided at the user mobile device 110, and/or the owner and/or the user mobile device 110 may initiate transmitting the request in response to a receiving a request at the user mobile device 110 for permission to access the data record (process block 152).

In one embodiment, the healthcare provider 102 may identify user mobile devices 110 within a communication range or the geofenced area 116 that have an active medical records management application or program, such as application or program suitable to facilitate user interaction with the communication network 126, running in the background before transmitting the request. That is, for example, entry of the user mobile device 110 into the geofenced area may trigger, via the communication network 126, a handshake or other communication with the provider computing device 112 to identify the user mobile device 110. The identification in turn causes the healthcare provider 102 associated with the geofenced area 116 to transmit the request to the distributed file system 104 such that the request is associated with the patient 108 via the identification information stored in the application of the user mobile device 110.

In any case, the request may include information related to the healthcare provider 102, the patient 108, the data record, and/or the like. In some embodiments, the request may include information related to the location of the healthcare provider 102, which may include an IP address associated with the provider computing device 112, a service set identifier (SSID) associated with the provider computing device 112, a basic service set identifier (BSSID) associated with the provider computing device 112, a communication network, such as a Wi-Fi network accessed by the provider computing device 112, and/or an address specified by the healthcare provider 102. Further, in some embodiments, the request may include information related to the location of the user mobile device 110, which may be determined based in part on one or more sensors, such as a GPS sensor and/or an altimeter, associated with the user mobile device 110.

After receiving the request to permit access by the healthcare provider 102 to the data record, the location associated with the provider may be identified (process block 184). In some embodiments, for example, the location of the healthcare provider 102 may be identified based in part on the information included in the request, as described above. While the IP address and/or other location information associated with the healthcare provider 102 may be included in the request, in some embodiments, the IP address and/or other location information may be obtained from the provider computing device 112 by pinging the provider computing device 112 for the information. Further, in some embodiments, the provider computing device 112 may be a user mobile device 110 associated with the healthcare provider 102. In such embodiments, the location of the healthcare provider 102 may be determined based on information determined by a GPS sensor included in the provider computing device 112. Moreover, the location associated with the healthcare provider 102 may be determined based on a stored mapping, such as a table, dictionary, key-value pair, and/or another suitable data structure, of information identifying the healthcare provider 102 (e.g., a name, a unique identifier, and/or the like) to the location associated with the healthcare provider 102.

Further, as described with reference to FIG. 1, the location associated with the healthcare provider 102 may represent a geofenced area 116, which may encompass the healthcare provider 102 and an area surrounding the healthcare provider 102. In some embodiments, the boundary (e.g., geofence) of the area surrounding the healthcare provider 102 may be determined automatically based on a default radius (e.g., 100 yards) from the location associated with the healthcare provider 102 and/or based on the accuracy (e.g., sensitivity) of the method used to determine the location of the healthcare provider 102. Additionally or alternatively, the patient 108 may set the boundary of the area surrounding the healthcare provider 102, which in some embodiments, may be stored in a mapping of the information identifying the healthcare provider 102 to the boundary of the area surrounding the healthcare provider 102.

The method 180 further includes identifying the location of the user mobile device 110 associated with the owner (e.g., patient 108) of the data record (process block 186). In some embodiments, the location of the user mobile device 110 may be identified based on information included in the request to permit access by the healthcare provider 102 to the data record. Additionally or alternatively, the location of the user mobile device 110 may be determined based on information, such as a GPS location determined by a GPS sensor located within the user mobile device 110. While the GPS location may be included in the information included in the request, in some embodiments, the GPS location may be requested and received directly from the user mobile device 110 and/or the GPS sensor. Further, in some embodiments, the location of the user mobile device 110 may be determined based on information, such as altitude, determined by an altimeter and/or a barometer associated with the user mobile device 110. In such cases, for example, the location of the user mobile device 110 may be determined or estimated to be on a certain floor (e.g., level) within a building.

After identifying the location of both the healthcare provider 102 and the user mobile device 110, the blockchain node 122 may determine whether the location of the user mobile device 110 is within the geofenced area 116 corresponding to the healthcare provider 102 (process block 188). That is, for example, the location of the user mobile device 110 may be compared to the geofenced area 116 corresponding to the healthcare provider 102. In some embodiments, comparing the location of the user mobile device 110 to the geofenced area 116 may involve converting the location of the user mobile device 110 and/or the location corresponding to the geofenced area 116 to a suitable format (e.g., longitude and latitude coordinates, GPS coordinates, a mailing address format, and/or the like) and determining that the user mobile device is within the geofenced area 116 and or is within a predetermined threshold distance relative to an outer boundary of the geofenced area 116 (e.g., less than 100 meters away).

If the location of the user mobile device 110 is determined to be outside the geofenced area 116 corresponding to the healthcare provider 102, the request to permit access by the healthcare provider 102 may be denied (process block 190). In such cases, the healthcare provider 102 may be blocked from subsequent attempts to access the data record. Further, as described above, a notification may be transmitted to the provider computing device 112 to convey to the healthcare provider 102 that the request has been denied.

If, on the other hand, the location of the user mobile device 110 is determined to be within the geofenced area 116, a biometric confirmation request may be transmitted to the owner (e.g., user mobile device 110 associated with the owner) of the data record (process block 192). In response to receiving the biometric confirmation request, the user mobile device 110 may prompt the owner to provide a biometric confirmation, such as a fingerprint scan, a voice recognition scan, a facial scan, an eye scan and/or the like, to validate permitting access by the healthcare provider 102 to the data record.

Accordingly, after transmitting the biometric confirmation request to the owner, a response to the biometric confirmation request may be received from the user mobile device 110 (process block 194). Based on this response, the distributed file system 104 (e.g., the blockchain node 122) may determine whether the request is validated (process block 196). That is, for example, the blockchain node 122 may determine whether the user provided the biometric confirmation within a specified time period. After the time period has elapsed, if no response to the biometric confirmation request has been received, the blockchain node 122 may determine that the owner failed to validate the request. If, on the other hand, a biometric confirmation is received within the time period, the blockchain node 122 may determine whether the biometric confirmation is valid. In the case of a finger print scan, for example, the blockchain node may determine whether the biometric confirmation is valid by comparing the fingerprint scan to a stored fingerprint scan associated with the owner. Additionally or alternatively, the user mobile device 110 may determine whether a biometric confirmation has been received within the time period and/or whether a received biometric confirmation is valid. In such cases, the user mobile device 110 may include such information in the response. Accordingly, the blockchain node 122 may determine whether the request to permit access is validated based on the information included in the response to the biometric confirmation request.

If the request to permit access by the healthcare provider 102 is not validated, the request may be denied (process block 190). If, on the other hand, the request is validated, the healthcare provider 102 may be permitted to access the data record (process block 198). More specifically, as discussed above, the blockchain node 122 may transmit and/or associated a public key and/or a private key with the healthcare provider 102, provide a reference to the data record and/or a blockchain 124 that includes the data record, transmit a notification to the provider computing device 112, or a combination thereof. Further, the blockchain node 122 may transmit a notification to the user mobile device 110 to confirm that access to the data record has been granted to the healthcare provider 102.

Figure 5:
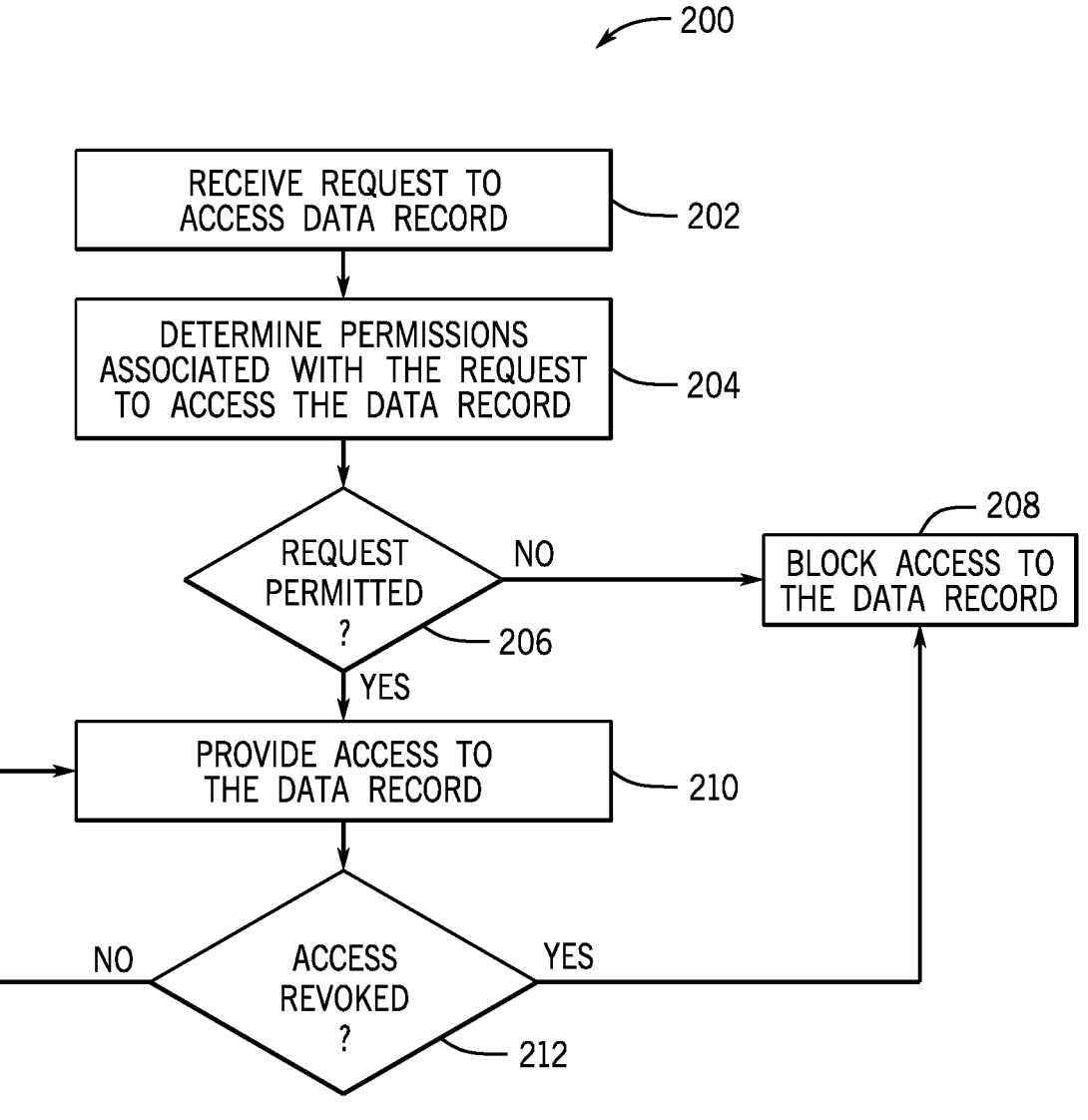
FIG. 5 is a flow diagram of a method for accessing a data record stored in the distributed file system of FIG. 2, in accordance with embodiments described herein.

Turning now to FIG. 5, a method 200 for accessing a data record is illustrated. Although the following description of the method 200 is described in a particular order, which represents a particular embodiment, it should be noted that the method 200 may be performed in any suitable order. Further, certain steps may be skipped altogether, and additional steps may be included in the method 200. Moreover, although the following description of the method 200 is described as being performed by a blockchain node 122, it should be noted that the method 200 may be performed by any other implementation of a distributed file system 104 or any suitable computing device. More specifically, in some embodiments, the method 200 may be implemented by a processor, which is understood to include one or more processors.

In any case, the blockchain node 122 may receive a request to access a data record (process block 202). The request may be received from the user mobile device 110 so that, for example, the owner (e.g., patient 108) of the data record may access the data record. Additionally or alternatively, the request may be received from the provider computing device 112 so that the healthcare provider 102 may access the data record. Further, in some embodiments, the request may include information related to the requestor (e.g., the owner and/or the healthcare provider 102), a device associated with the requestor (e.g., the user mobile device 110 and/or the provider computing device 112, respectively), and/or to the data record. That is, for example, the request may include information identifying the requestor, information identifying the device associated with the requestor, information identifying the data record, information related to permissions associated with the requestor to access data in the distributed file system 104, and/or the like. Further, information identifying the requestor and/or the information identifying the device associated with the requestor may be determined by the user mobile device 110, the provider computing device 12, and/or within the communication network 126, based on, for example, fast identity online (FIDO) authentication.

After receiving the request to access the data record, the blockchain node 122 may determine permissions associated with the request to access the data record (process block 204). That is, for example, based on the information included in the request, such as the information identifying the requestor and/or the permissions associated with the requestor, the blockchain node 122 may determine permissions associated with the request. In some embodiments, the blockchain node 122 may additionally or alternatively determine the permissions associated with the request based on a stored mapping of information identifying the requestor to permissions associated with the requestor and/or the data record. In any case, as discussed above, the permissions may identify whether read-only access, read-write access, and/or the like of the data record may be provided to the requestor. Further, the permissions may be ephemeral permissions, which may expire in response to detection of an event, as described above.

After determining the permissions associated with the request, the blockchain node 122 may determine whether the request is permitted (process block 206). In some embodiments, for example, the blockchain node 122 may determine whether the permissions associated with the request are adequate to grant access to the data record. More specifically, if the request to access the data record is a read-only request, suitable permissions associated with the request to grant access to the data record may include read-only access permissions and/or read-write access permissions, while only read-write access permissions may be suitable for a request to write to the data record. Further, as the permissions and/or access granted to a healthcare provider 102 may be ephemeral based on a time period, a number of instances of access to the data record, and/or the geographic location of the user mobile device 110, the request may not be permitted if the access to the data record by the healthcare provider 102 has been revoked and/or the permissions associated with the healthcare provider 102 are not currently valid, as described in greater detail below.

If the request is determined to not be permitted, access to the data record may be blocked (process block 208). If, on the other hand, the request is determined to be permitted (process block 210), the blockchain node 122 may provide access to the data record. To do so, the blockchain node 122 may provide a reference, such as a pointer, to the data record, which may be stored in a blockchain 124, to the requestor. Accordingly, in some embodiments the blockchain node 122 may provide a pointer to a blockchain 124 and/or a portion of a blockchain 124 that contains the data record to the requestor. Additionally or alternatively, the blockchain node 122 may provide raw data included in the data record. For example, in some embodiments, the blockchain node 122 may store a copy of the blockchain 124 on the device associated with the requestor, such as the user mobile device 110 and/or the provider computing device 112.

After the blockchain node 122 permits access by a healthcare provider 102 to a data record, the blockchain node 122 may determine whether the permissions to access the data record by the healthcare provider 102 are revoked (process block 212). That is, for example, the blockchain node 122 may determine whether any ephemeral permissions granted to the healthcare provider 102 have expired and/or whether a request from the user mobile device 110 removing the permissions granted to the healthcare provider 102 has been received. In some embodiments, the blockchain node 122 may poll for an event associated with the expiration of the ephemeral permissions at a regular interval. Accordingly, in some embodiments, the blockchain node 122 may periodically determine whether a time period associated with the ephemeral permissions has elapsed and/or whether the location of the user mobile device 110 is within the geofenced area 116 associated with the healthcare provider 102. Additionally or alternatively, an occurrence of an event associated with the expiration of the ephemeral permissions may automatically trigger the blockchain node 122 to revoke access by the healthcare provider 102 to the data record. For example, in some embodiments, the user mobile device 110 may notify the blockchain node 122 that the location of the user mobile device 110 is no longer within the geofenced area 116 associated with the healthcare provider. Further, in some embodiments, before each instance of access by the healthcare provider 102 to the data record, the blockchain node 122 may determine whether the total instances of access by the healthcare provider 102 to the data record exceeds a set number of instances of access by the healthcare provider 102 to the data record.

In any case, after determining that access by the healthcare provider 102 to the data record has been revoked, the blockchain node 122 may block access by the healthcare provider 102 to the data record (process block 208). As access may be revoked at any suitable time, in some embodiments, blocking access by the healthcare provider 102 to the data record may involve interrupting access by the healthcare provider 102 to the data record. Accordingly, in some embodiments, regardless of whether the healthcare provider 102 is actively accessing and/or modifying the data record, the blockchain node 122 may revoke access by the healthcare provider 102 to the data record.

While only certain features of disclosed embodiments have been illustrated and described herein, many modifications and changes will occur to those skilled in the art. It is, therefore, to be understood that the appended claims are intended to cover all such modifications and changes as fall within the true spirit of the present disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform] ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A method performed by at least one processor, the method comprising:
   receiving, at a blockchain node of a distributed file system comprising one or more records associated with a user, a request to permit access to a record of the one or more records by a service provider, wherein the request comprises a record identifier associated with the record, an indication of a location of the service provider, and an indication of a mobile device associated with an owner of the record, and wherein the one or more records are stored in a blockchain of the blockchain node by a series of immutable transactions;
   identifying the record stored in the blockchain based on the record identifier;
   determining a geofenced area associated with the service provider based on the indication of the location of the service provider, wherein the geofenced area corresponds with an area encompassing a geographic location associated with the service provider;
   querying a location of the mobile device;
   determining that the mobile device is within the geofenced area associated with the service provider;
   in response to entry of the mobile device in the geofenced area, identifying the mobile device as being associated with the user, wherein the identifying is based on a handshake between the mobile device and the service provider with an application running and active on the mobile device to facilitate user interaction with a communication network of the service provider;
   sending a biometric confirmation request to the mobile device for a biometric confirmation to permit the service provider access to the record based upon determining that the mobile device is within the geofenced area and identifying that the mobile device is associated with the user;
   receiving the biometric confirmation from the mobile device;
   upon receiving the biometric confirmation, determining validation of the request to permit access to the record, wherein the validation comprises receiving the biometric confirmation within a specified time period; and
   upon determining the validation, transmitting the record or a reference to the record from the blockchain to a service provider device associated with the service provider according to permission information associated with the record.

2. The method of claim 1, wherein the permission information comprises ephemeral permissions that expire after a pre-determined amount of time such that the service provider cannot access the record or the reference to the record after the pre-determined amount of time has passed.

3. The method of claim 1, wherein the permission information comprises permissions that expire after a pre-determined number of uses such that the service provider cannot access the record or the reference to the record after the pre-determined number of uses has been exceeded.

4. The method of claim 1, comprising transmitting a key to the service provider device and transmitting the record or the reference to the record in response to receipt of the key.

5. The method of claim 4, comprising, prior to transmitting the record or the reference to the record, decrypting the record or the reference to the record based in part on the key.

6. The method of claim 1, wherein transmitting the record or the reference to the record from the blockchain to the service provider device associated with the service provider comprises:

transmitting a key to the service provider device;

receiving an additional request from the service provider device to access the one or more records associated with the user, wherein the additional request comprises the key;

determining, based in part on the key and the permissions information, whether the additional request is permitted; and when the additional request is permitted:

transmitting the record or the reference to the record from the blockchain to the service provider device associated with the service provider; and when the additional request is not permitted:

outputting a notification to the service provider device associated with the service provider that access to the one or more records or the reference to the one or more records has been denied.

7. The method of claim 1, comprising, after transmitting the record or the reference to the record from the blockchain to the service provider device associated with the service provider:

receiving, at the blockchain node, additional location information of the mobile device;

determining that the mobile device is outside the geographic location associated with the service provider based on the additional location information of the mobile device; and revoking access by the service provider to the record or the reference to the record.

8. The method of claim 1, wherein the one or more records are an electronic medical record of the user.

9. The method of claim 1, wherein the one or more records are selected from a plurality of user-associated records based on the permission information.

10. The method of claim 1, wherein the one or more records are stored as hashed record data in an interplanetary file system, and wherein the record identifier comprises a hash address associated with a respective portion of the hashed record data.

11. The method of claim 1, wherein the one or more records are owned by the user and stored in the distributed file system.

12. A distributed file system, comprising:

a blockchain node comprising one or more records associated with a user, wherein the one or more records are stored in a blockchain of the blockchain node by a series of immutable transactions; and a processor configured to:

receive a request to permit access to a record of the one or more records by a service provider, wherein the request comprises a record identifier associated with the record, an indication of a location of the service provider, and an indication of a mobile device associated with an owner of the record;

identify the record stored in the blockchain based on the record identifier;

determine a geofenced area associated with the service provider based on the indication of the location of the service provider, wherein the geofenced area corresponds with an area encompassing a geographic location associated with the service provider;

query a location of the mobile device;

determine that the mobile device is within the geofenced area associated with the service provider;

in response to entry of the mobile device in the geofenced area, identify the mobile device as being associated with the user, wherein the identifying is based on a handshake between the mobile device and the service provider with an application running and active on the mobile device to facilitate user interaction with a communication network of the service provider;

send a biometric confirmation request to the mobile device for a biometric confirmation to permit the service provider access to the record based upon the determination that the mobile device is within the geofenced area and the identification that the mobile device is associated with the user;

receive the biometric confirmation from the mobile device;

upon receiving the biometric confirmation, transmit the record or a reference to the record from the blockchain to a service provider device associated with the service provider according to permission information associated with the record;

receive an updated request to permit access to the record of the one or more records by the service provider;

receive updated location information of the mobile device;

determine that the mobile device is outside the geographic location associated with the service provider based on the updated location information of the mobile device;

denying access by the service provider to the record or the reference to the record; and transmitting a notification to the service provider that the request has been denied.

13. The distributed file system of claim 12, wherein the mobile device comprises a global positioning system (GPS) sensor, wherein the location of the mobile device is based in part on GPS location information determined by the GPS sensor.

14. The distributed file system of claim 12, wherein the mobile device comprises a fingerprint scanner, wherein the biometric confirmation comprises a fingerprint associated with the user.

15. The distributed file system of claim 12, wherein the mobile device comprises a camera, wherein the biometric confirmation comprises a facial scan, an eye scan, or a combination thereof, associated with the user.

16. The distributed file system of claim 12, wherein the request comprises a hypertext transfer protocol (HTTP) request.

17. A tangible, non-transitory, machine-readable medium, comprising machine-readable instructions which, when executed, cause at least one processor to perform operations comprising:

receiving, at a blockchain node of a distributed file system comprising one or more records associated with a user, a request to permit access to a record of the one or more records by a service provider, wherein the request comprises a record identifier associated with the record, an indication of a location of the service provider, and an indication of a mobile device associated with an owner of the record, and wherein the one or more records are stored in a blockchain of the blockchain node by a series of immutable transactions;

identifying the record stored in the blockchain based on the record identifier;

determining a geofenced area associated with the service provider based on the indication of the location of the service provider, wherein the geofenced area corresponds with an area encompassing a geographic location associated with the service provider;

querying a location of the mobile device;

determining that the mobile device is within the geofenced area associated with the service provider;

in response to entry of the mobile device in the geofenced area, identifying the mobile device as being associated with the user, wherein the identifying is based on a handshake between the mobile device and the service provider with an application running and active on the mobile device to facilitate user interaction with a communication network of the service provider;

transmitting a biometric confirmation request to the mobile device for a biometric confirmation to permit the service provider access to the record based upon determining that the mobile device is within the geofenced area and identifying that the mobile device is associated with the user;

receiving the biometric confirmation from the mobile device;

upon receiving the biometric confirmation, transmitting the record or a reference to the record from the blockchain to a service provider device associated with the service provider according to permission information associated with the record;

determining a pre-determined amount of time has passed; and revoking access by the service provider to the record or the reference to the record.

18. The tangible, non-transitory, machine-readable medium of claim 17, wherein the operations comprise:

determining the geofenced area based in part on an internet protocol (IP) address of the service provider device, a basic service set identifier (BSSID) of the service provider device, a service set identifier (SSID) of the service provider device, a communication network accessed by the service provider device, or a combination thereof.

19. The tangible, non-transitory, machine-readable medium of claim 17, wherein the operations comprise:

receiving an additional request from the service provider device to access the record;

querying the location of the mobile device associated with the user to obtain location information of the mobile device;

determining that the mobile device is not within the geofenced area associated with the service provider based on the location information of the mobile device;

denying access by the service provider to the record based in part on the location information of the mobile device; and outputting a notification to the service provider device.

20. The tangible, non-transitory, machine-readable medium of claim 17, wherein the operations comprise:

receiving an additional request from the service provider device to access additional records associated with the user;

determining, based on information related to the additional records, that the service provider lacks permission to access the additional records;

denying access by the service provider to the additional records based in part on the information related to the additional records; and outputting a notification to the service provider device.

* * * * *